US00PP30260P3

(12) United States Plant Patent
Carrieres

(10) Patent No.: US PP30,260 P3
(45) Date of Patent: Mar. 5, 2019

(54) APPLE TREE NAMED 'XELEVEN'

(50) Latin Name: ***Malus domestica* Borkh.**
Varietal Denomination: Xeleven

(71) Applicant: Red Moon, Srl, Bolzano (IT)

(72) Inventor: Jean-Luc Carrieres, Bolzano (IT)

(73) Assignee: Red Moon, SRL, Bolzano (IT)

( * ) Notice: Subject to any disclaimer, the term of this patent is extended or adjusted under 35 U.S.C. 154(b) by 0 days.

(21) Appl. No.: 15/731,348

(22) Filed: May 30, 2017

(65) Prior Publication Data

US 2018/0352693 P1 Dec. 6, 2018

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
See application file for complete search history.

*Primary Examiner* — Susan McCormick Ewoldt
(74) *Attorney, Agent, or Firm* — Michelle Bos Legal LLC

(57) ABSTRACT

'Xeleven' is a new and distinct apple tree notable for its semi-upright plant habit, red skin over color, scab resistance and mid-late timing of fruit ripening.

4 Drawing Sheets

Latin name: *Malus domestica* Borkh.
Variety denomination: 'Xeleven'.

BACKGROUND OF THE VARIETY

The present invention relates to a new and distinct cultivar of apple tree, (*Malus domestica* Borkh.), and hereinafter referred to by the name 'Xeleven'.

The new apple variety 'Xeleven' originated in Lot, France as an open-pollination of female parent (('Esopus Sptizenberg Op.' x 'PRI 612-1') x 'Gala') (not patented) by an unknown male parent. The new apple tree was discovered and selected by the inventor as a single plant from within the progeny of the stated open-pollination in a controlled environment in Lot, France in 1994.

Asexual reproduction of the new apple tree by budding and grafting, beginning in 2004 in Lot, France, has demonstrated that the new variety reproduces true to type with all of the distinguishing characteristics, firmly fixed and retained through successive generations.

BRIEF DESCRIPTION OF THE VARIETY

The following characteristics of the new variety have been repeatedly observed and can be used to distinguish 'Xeleven' as a new and distinct variety of apple tree:

1. Semi-upright plant habit.
2. Red skin over color.
3. Mid to late timing of fruit ripening.
4. Yellow flesh color.

Fruit of 'Xeleven' is distinguished from fruit of its female parent by its earlier harvest maturity, higher sugar content, increased vigor and improved storageability. Fruit of 'Xeleven' is distinguished from similar variety 'PRI 612-1' (not patented) by its later harvest date, very firm flesh, higher sugar level, a complex tropical flavor, and very long storageability. A comparison of 'Xeleven' to 'PRI 612-1' and 'Golden Delicious' (not patented) is set forth in Table 1 below.

TABLE 1

| | 'Xeleven' | 'PRI 612-1' | 'Golden Delicious' |
|---|---|---|---|
| Flowering time | Medium-Late | Medium | Medium |
| Vigor | Medium | Strong | Medium |
| Harvesting time | 5 weeks after 'Golden Delicious' | 2 weeks before 'Golden Delicious' | Mid-September |
| Pressure kg/cm$^2$ | 9.9 to 10.3 | 8.5 to 9.5 | 6.6 to 7.0 |
| IR ° Brix | 14.0 to 15.0 | 11.1 to 12.2 | 11.5 to 13.0 |
| Acidity | 7.8 g/L MA | 5.7 to 6.1 g/L MA | 3.8 to 5.1 g/L MA |
| Storage | Very Good | Medium | Good |

BRIEF DESCRIPTION OF THE PHOTOGRAPHS

Figure 1:
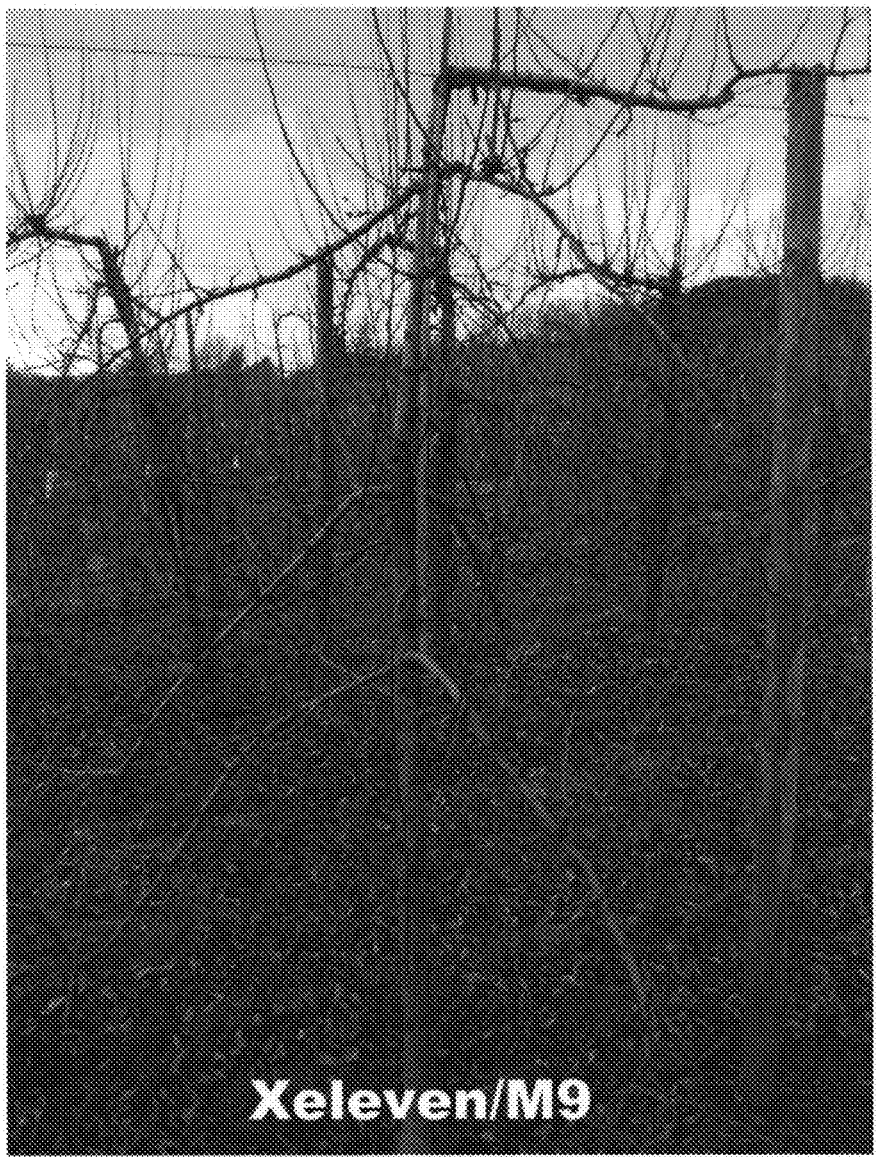
Figure 2:
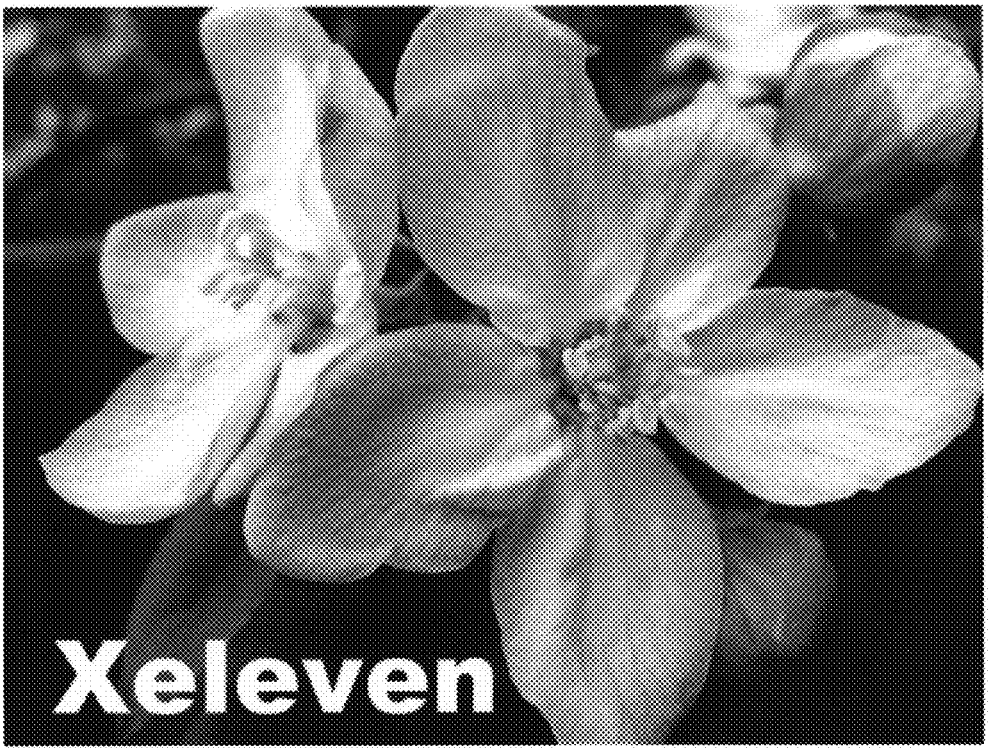
Figure 3:
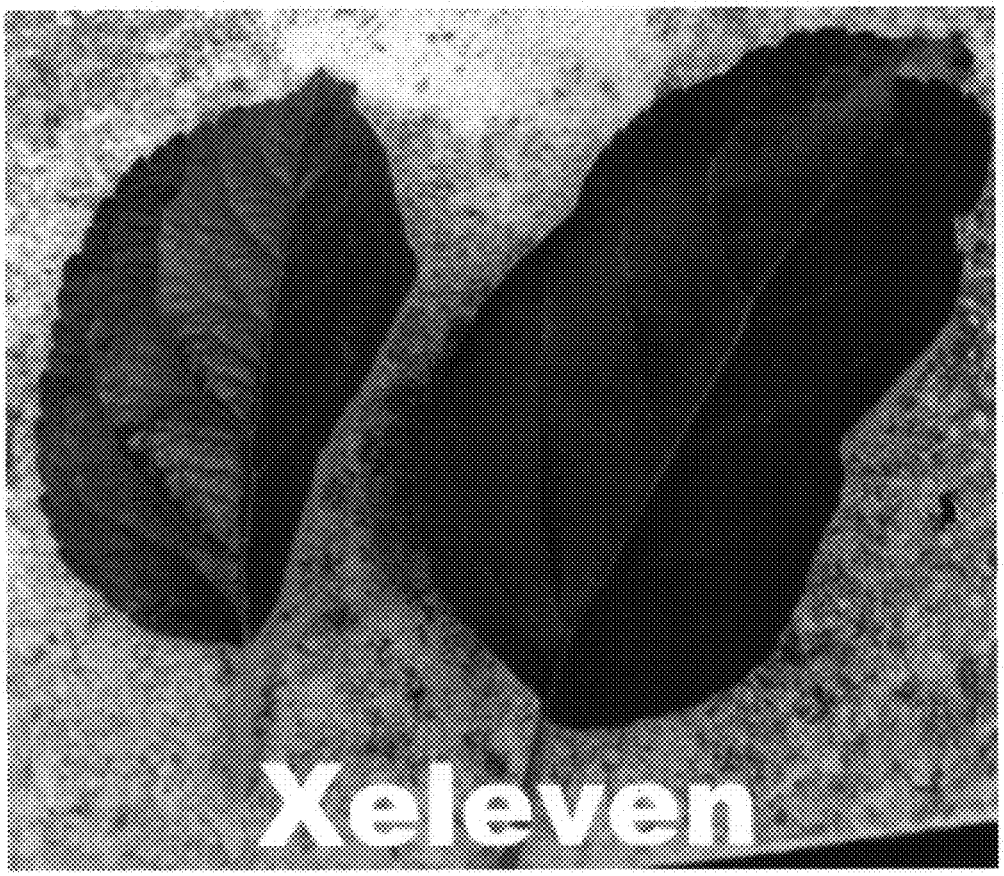
Figure 4:
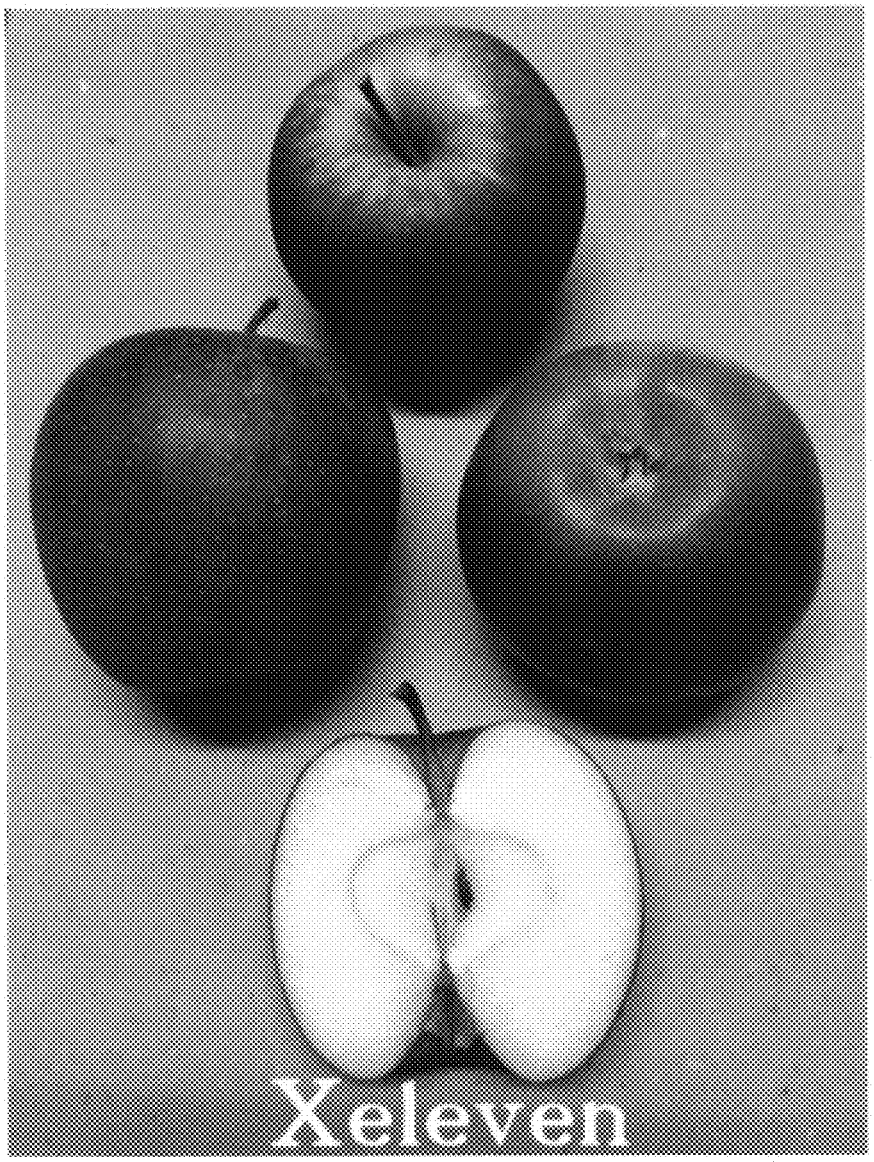

FIG. 1 shows the tree of the new variety;
FIG. 2 shows a flower of the new variety;
FIG. 3 shows leaves of the new variety; and
FIG. 4 shows whole and sectioned fruit of the new variety;

DETAILED BOTANICAL DESCRIPTION OF THE VARIETY

The following detailed botanical description is based on observations of trees grown on 'M9' rootstock (not patented) and planted in 2005. Observations were recorded during the 2014 and 2015 growing seasons at Lot, France. Color descriptions refer to The Royal Horticultural Society Colour Chart (1995). It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree:
*Vigor*.—Vigorous.
*Habit*.—Semi-Upright.
*Height*.—2.9 m.
*Bearing*.—On spurs and long shoots.
Trunk:
*Diameter*.—17-21 cm at 30 cm above graft union.
*Bark texture*.—Smooth.
*Bark color*.—Brown RHS N200C.
Branches-1 m above graft union:
*Length*.—160 cm.
*Diameter*.—7.0 cm.
*Crotch angle*.—60°.
*Color*.—Moderate brown N200D.
Dormant one year old shoot:
*Diameter*.—5-6 mm.
*Length*.—25-30 cm.
*Color*.—Brown 200C.
*Internode length*.—2.0 cm.
*Pubescence*.—Few.
*Lenticels*.—Size 1-2 mm, density 1 to 2 $cm^2$.
Flowers:
*Bud*.—Quantity per spur 4 to 5; length 5-7 mm; shape elongated; color pale purplish pink 61D.
Petals:
*Quantity per flower*.—5.
*Relative position of petal margins*.—Free to touching.
*Margins*.—Entire.
*Apex shape*.—Round.
*Base shape*.—Round.
*Length*.—14 to 16 mm.
*Width*.—13 to 14 mm.
*Upper surface color*.—White 155D.
*Lower surface color*.—Pale pink 49D.
Flower:
*Diameter of fully open flower*.—2.8 cm to 3.0 cm.
*Quantity per cluster*.—5.
*Bloom period*.—Mid- to late season; first bloom April 14, full bloom April 22 at Lot, France.
*Pollination requirement*.—Pollinator required; 'Golden Delicious' or comparable.
Sepals:
*Quantity per flower*.—5.
*Length*.—4 mm.
*Width*.—2 mm.
*Shape*.—Triangular.
*Color*.—Green 135A.
Pedicel:
*Length*.—18 to 20 mm.
*Diameter*.—1.8 mm.
*Color*.—Light green 132D.
Pistil:
*Length*.—10 to 12 mm.
*Color*.—Yellow-green 145C.
Anthers:
*Quantity per flower*.—16.
*Length*.—2 mm.
*Pollen color*.—Yellow 12B.
Stigma:
*Size*.—1 mm.
*Color*.—Yellow 11C.
Style:
*Length*.—6 mm.
*Color*.—Yellow-green 145C.
Leaf:
*Attitude in relation to shoot*.—Outward.
*Arrangement*.—Opposite.
*Size*.—Length 9 to 10 cm.
*Width*.—4.5 to 5.0 cm.
*Length to width ratio*.—1.8 to 2.0.
*Margin*.—Serrate.
*Color upper surface*.—Green 131A.
*Color lower surface*.—Green 132A.
*Shape*.—Ovate; apex acuminate; base equilateral.
Petiole:
*Length*.—1.6 to 2.0 cm.
*Width*.—2 mm.
*Color*.—Yellow-green 143A.
Fruit:
*Weight*.—150 to 180 g.
*Diameter*.—75 to 90 mm.
*Height*.—75 to 90 mm.
*Fruit shape*.—Cylindrical.
*Position of maximum diameter*.—Top.
*Ribbing*.—Absent.
*Aperture of eye*.—Closed.
*Depth of eye basin*.—6 to 8 mm.
*Width of eye basin*.—25 to 30 mm.
*Stalk diameter*.—2.5 mm.
*Stalk length*.—18 to 24 mm.
*Stalk color*.—Brown 200B.
*Depth of stalk cavity*.—12 to 14 mm.
*Width of stalk cavity*.—19 mm.
*Lenticel size*.—0.5 to 0.7 mm.
*Lenticel density*.—8 to 10 per $cm^2$.
*Bloom of skin*.—Minimal.
*Greasiness of skin*.—Absent.
*Ground color of skin*.—Red 47A.
*Over color of skin*.—Pink-red 46A.
*Amount of over color*.—90 percent.
*Pattern of over color*.—Solid flush.
*Flesh texture*.—Fine, firm.
*Flesh firmness*.—Firm, about 10.5 $kg/cm^2$.
*Flesh color*.—Pale yellow 8D.
*Aroma*.—Complex.
Seeds:
*Quantity per fruit*.—8 to 10.
*Shape*.—Teardrop.
*Color*.—Brown 200B.
*Harvest date*.—Mid-October at Lot, France.
Resistance/susceptibility to known diseases/pests: Scab resistant, mildew resistant.
*Market use*.—Fresh and processor.
*Yield*.—15 to 20 kg to tree.

The invention claimed is:

1. A new and distinct apple tree as described and illustrated herein.

* * * * *